United States Patent [19]  [11]  4,365,067
Fujimoto et al.  [45]  Dec. 21, 1982

[54] METHOD FOR PREPARING PHARMACOLOGICALLY ACTIVE CYANOGUANIDINE DERIVATIVE

[75] Inventors: Michitaro Fujimoto, Tondabayashi; Takaichi Fukui, Nara; Toshimitsu Mozai, Habikino; Yoshikazu Funazo, Toyonaka, all of Japan

[73] Assignee: Fujimoto Pharmaceutical Corporation, Japan

[21] Appl. No.: 324,017

[22] Filed: Nov. 23, 1981

[30] Foreign Application Priority Data

Nov. 26, 1980 [JP] Japan .................................. 55-166028

[51] Int. Cl.$^3$ ........................................... C07D 233/64
[52] U.S. Cl. ................................................. 548/342
[58] Field of Search ........................................ 548/342

[56] References Cited

U.S. PATENT DOCUMENTS 4,093,621  6/1978  Brown et al. ........................ 548/342
4,200,761  4/1980  Jenko et al. ......................... 548/342

Primary Examiner—Robert W. Ramsuer
Attorney, Agent, or Firm—Omri M. Behr

[57] ABSTRACT

A pharmacologically active cyanoguanidine derivative, generally referred to as cimetidine, is prepared by causing 4-methyl-5-hydroxymethylimidazole or a salt thereof to react with 2-substituted-1-methyl pyridinium salt and then causing the intermediate reaction product to react with N-cyano-N'-methyl-N"-(2-melcaptoethyl)-guanidine. The initial and subsequent reactions are carried out at room temperature under atmospheric pressure, using one and the same reaction vessel. No isolation of the intermediate reaction product resulting from the first reaction is required preparatory to the subsequent reaction. The recovery of the final intended product is carried out without using a column chromatography.

4 Claims, No Drawings

METHOD FOR PREPARING PHARMACOLOGICALLY ACTIVE CYANOGUANIDINE DERIVATIVE

BACKGROUND OF THE INVENTION

The present invention relates to a method for preparing a pharmacologically active cyanoguanidine derivative and, in particular, to a method for preparing N-cyano-N'-methyl-N''-[2-{(4-methyl-5-imidazolyl)-methylthio}-ethyl] guanidine which is represented by the following formula:

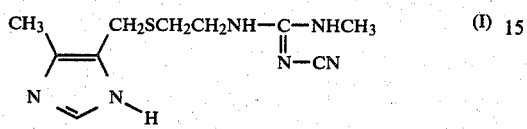

The compound with which the present invention is concerned is generally referred to as "cimetidine" and is pharmacologically useful in that the compound has an inhibiting action to the histamine-H$_2$-receptor.

Various methods for the preparation of the compound of the formula (I) above have heretofore been proposed such as disclosed in, for example, Japanese Laid-open Patent Publication No. 49-75574 (corresponding to United Kingdom Patent Applications No. 41160/1972 and No. 6154/1973), laid open to public inspection in 1974, and Japanese Laid-open Patent Publication No. 51-125074 (corresponding to United Kingdom Patent Application No. 38257/1974) laid open to public inspection in 1976. According to these publications, the prior art methods are complicated and time-consuming in that they require a plurality of reaction processes to be performed with the consequent repetition of isolation and purification of the respective intermediate reaction products. More specifically, each intermediate reaction product resulting from one reaction process is required to be isolated or purified before it is subjected to the subsequent reaction process. Recovery of the final intended product involves the employment of a column chromatography to effect the isolation and/or purification. Not only is the column chromatography expensive and costly, but the employment of the column chromatography requires the subsequent condensation of the diluted solution obtained therefrom. In addition, the known methods give a relatively low yield of approximately 30%.

SUMMARY OF THE INVENTION

Accordingly, the present invention has been developed with a view to substantially eliminating the disadvantages and inconveniences inherent in the prior art methods and has for its essential object to provide an improved method for preparing cimetidine of the formula (I) above, which method is featured in that a plurality of reaction processes are carried out in one and the same reaction vessel with no need of the isolation or purification of the respective intermediate products to be performed preceding the subsequent reaction.

Another important object of the present invention is to provide an improved method of the kind referred to above, wherein no column chromatography is required in recovering the final intended reaction product.

A further important object of the present invention is to provide an improved method of the kind referred to above, which can give a relatively high yield of the final intended product.

According to the present invention, the intended final product, i.e., the cimetidine of the formula (I) above, can be obtained in a relatively short period of time by using relatively readily available raw materials and by the employment of readily available reaction conditions.

More specifically, according to the present invention, the intended final product can be obtained by reacting 4-methyl-5-hydroxymethylimidazole, represented by the following formula;

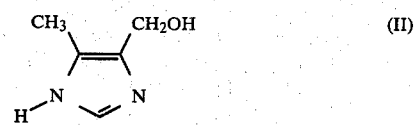

or a salt thereof, preferably the hydrochloride, with a 2-fluoro-1-alkyl pyridinium salt, represented by the following general formula;

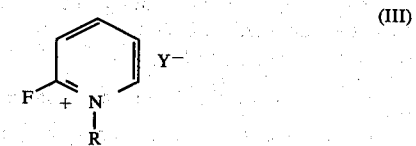

wherein R is methyl or ethyl and Y$^-$ is an acid residue, preferably the p-toluenesulfonic acid residue, to produce an intermediate, but unisolated reaction product which is subsequently caused to react with N-cyano-N'-methyl-N''-(2-melcaptoethyl)-guanidine represented by the following formula;

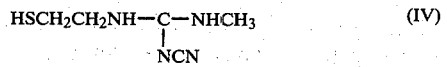

DESCRIPTION OF PREFERRED EMBODIMENTS

Both the initial reaction of the compound of the formula (II) with the compound of the formula (III) and the subsequent reaction of the intermediate unisolated reaction product with the compound of the formula (IV) may be carried out in the presence of a reaction-inert organic solvent, suitably a polar nonhydroxylic organic solvent, such as chloroform, acetonitrile or any other such solvent known to those skilled in the art. Preferably, the reaction is carried out at ambient temperature (preferably within the range of 0° to 40° C.) and atmospheric pressure under a dry atmosphere full of inert gas such as nitrogen or any other inert gas known to those skilled in the art. In particular, the initial reaction of the compound of the formula (II) with the compound of the formula (III) can be facilitated by the presence of tertiary amine, for example, triethylamine or pyridine.

The molecular ratio of the compound of the formula (II) to the compound of the formula (III) is preferred to be within the range of approximately 1:1.1 to 1:1.5.

Moreover, according to the present invention, initial and subsequent reactions may be performed in a single reaction vessel. In addition, the intermediate compound resulting from the initial reaction need not be isolated or purified prior to the subsequent reaction, in contrast to the prior art methods wherein the isolation and/or purification of the intermediate reaction products are required. Yet, both of the reactions can be carried out under readily available reaction conditions, i.e., at room temperature and without the reaction vessel being pressurized.

In contrast to the starting material employed in the practice of the prior art methods, which is generally 4-methyl-5-chloromethyl imidazole, the starting material of the formula (II) employed in the practice of the present invention is chemically stable and, therefore, requires no strict and cumbersome care in handling.

Because of the features which have been described hereinabove, and will readily be understood from the subsequent description, as residing in the method of the present invention, the method of the present invention is effective to give a surprisingly higher yield, say, about 80 to 90%, than that afforded by the prior art methods.

DETAILED DESCRIPTION OF THE INVENTION

These and other objects and features of the present invention will become readily understood from the following detailed description taken in conjunction with illustrative examples.

Synthesis of Starting Material 2-fluoro-1-methylpyridinium tosylate is prepared by adding 18.6 g (0.1 mol.) of paratoluen sulphonate methyl ester to 9.7 g (0.1 mol.) of 2-fluoropyridine, heating the resultant mixture for about 20 minutes at 120° C. and cooling the heated mixture to yield 25 g of crystalline 2-fluoro-1-methylpyridinium tosylate (95%). This crystalline starting material is subsequently washed with ether and then dried.

EXAMPLE I

To a suspension of 4.47 g (0.03 mol.) of 4-methyl-5-hydroxymethylimidazole hydrochloride in 120 ml of chloroform is added 10 g of triethylamine. 8.5 g (0.032 mol.) of the 2-fluoro-1-methylpyridinium tosylate prepared in the manner described above is then added to the suspension, and the resultant mixture is subsequently stirred for 2 hours at room temperature under nitrogen atmosphere.

Thereafter, there is added to the reaction solution a solution 4.8 g of N-cyano-N'-methyl-N''-(2-mercaptoethyl) guanidine in 30 ml of chloroform and the mixture is then stirred for 6 hours at room temperature. 400 ml of aqueous sodium hydroxide is added to the reaction solution to adjust its pH value to 10, followed by the extraction with 400 ml of ethyl acetate. The resultant aqueous phase is further extracted with 300 ml of ethyl acetate. The ethyl acetate phases are combined together and then dried over anhydrous sulphate, the solvent being subsequently removed by evaporation under reduced pressure.

Trituration of the resultant residue with a small quantity of a mixed solvent consisting of acetonitrile, chloroform and n-hexane is carried out, followed by recrystallization from acetonitrile in a conventional manner to yield 6.2 g of the crystalline compound of the formula (I).

m.p. 139° to 141° C. Yield: 82.0%
(Found: C—47.8%; H—6.5%; and N—33.2%.

$C_{10}H_{16}N_6S$ requires: C—47.6%; H—6.4%; and N—33.3%)

In accordance with the above procedure but where, in place of triethylamine, there is utilized pyridine the same product is obtained.

EXAMPLE II

To a suspension of 4.47 g (0.03 mol.) of 4-methyl-5-hydroxymethylimidazole hydrochloride in 100 g of acetonitrile is added 2.4 g of pyridine, followed by the addition of 8.5 g (0.032 mol.) of the 2-fluoro-1-methylpyridinium tosylate prepared in the manner described above. The resultant mixture is stirred for 1.5 hours at room temperature under nitrogen atmosphere.

After the initial reaction, there is added to the reaction solution a solution of 4.8 g of N-cyano-N'-methyl-N''-(2-mercaptoethyl) guanidine dissolved in 50 ml of acetonitrile and the mixture is stirred for 8 hours at room temperature.

After the subsequent reaction, 300 ml of aqueous sodium hydroxide is added to the reaction solution to adjust its pH value to 10. The solution is subjected to extraction with 400 ml of ethyl acetate and then the aqueous phase is extracted with 300 ml of the same solvent. The resultant ethyl acetate phases are combined together and then dried, the solvent being subsequently removed by evaporation under reduced pressure.

The residue so obtained is triturated with a small quantity of water and the crude crystalline material so obtained is then recrystallized from acetonitrile in a conventional manner to yield 6.4 g of the crystalline compound of the formula (I).

m.p. 138° to 141° C. Yield: 84.7%

In accordance with the above procedure but where, in place of pyridine, there is utilized triethylamine, the same product is obtained.

Although the present invention has been described in detail in connection with the illustrative examples, it should be understood that such examples are only for the purpose of illustration and that various changes and modifications are, therefore, apparent to those skilled in the art from the disclosure of the present invention without departing from the spirit and scope of the present invention.

We claim:
1. A method for preparing a cyanoguanidine derivative which comprises the steps of:
 (a) reacting a 4-methyl-5-hydroxymethylimidazole or a salt thereof with a 2-fluoro-1-alkyl pyridinium salt, wherein alkyl is methyl or ethyl, to provide an intermediate product, and
 (b) reacting said intermediate reaction product with N-cyano-N'-methyl-N''-(2-mercaptoethyl)-guanidine to yield N-cyano-N'-methyl-N''-[2-{(4-methyl-5-imidazolyl)-methylthio}-ethyl] guanidine.
2. A method as claimed in claim 1, which comprises carrying out the step (a) in the presence of tertiary amine.
3. A method as claimed in claim 1, wherein either or both of the steps (a) and (b) are carried out at ambient temperature and atmospheric pressure.
4. A method as claimed in claim 1, 2 or 3, wherein either or both of the steps (a) and (b) are carried out in a reaction inert non-hydrocyclic poly organic solvent.

* * * * *